United States Patent [19]

Spurr

[11] Patent Number: 6,080,866
[45] Date of Patent: Jun. 27, 2000

[54] PROCESS FOR THE MANUFACTURE OF 2,5-DISUBSTITUTED PYRIDINES

[75] Inventor: Paul Spurr, Riehen, Switzerland

[73] Assignee: Hoffmann-La Roche Inc., Nutley, N.J.

[21] Appl. No.: 09/136,118

[22] Filed: Aug. 18, 1998

[30] Foreign Application Priority Data

Aug. 19, 1997 [EP] European Pat. Off. .............. 97114269

[51] Int. Cl.$^7$ ................................................. C07D 213/08
[52] U.S. Cl. ............................................. 546/250
[58] Field of Search ............................................. 546/250

[56] References Cited

U.S. PATENT DOCUMENTS 5,466,800 11/1995 Kraus ......................................... 544/82
5,837,708 11/1998 Breu et al. ............................... 514/274

FOREIGN PATENT DOCUMENTS

| 162 464 | 3/1989 | European Pat. Off. . |
| 584 491 | 5/1995 | European Pat. Off. . |
| 713 875 | 5/1996 | European Pat. Off. . |
| WO 96 19459 | 6/1996 | WIPO . |

*Primary Examiner*—D. Margaret Seaman
*Attorney, Agent, or Firm*—George W. Johnston; Dennis P. Tramaloni; Joseph P. Kirk, Jr.

[57] ABSTRACT

The present invention concerns a process for the preparation of a 2,5 disubstituted pyridine of the formula (I)

$$\text{(I)}$$

which comprises the steps of a) reacting a compound of the formula (II)

$$R^1\text{—CH}=\text{CH}\text{—}R^2 \quad \text{(II)}$$

with an acrylic compound of the formula (III)

$$\text{(III)}$$

to form a compound of the formula (IV)

$$\text{(IV)}$$

and b) reacting the compound of formula (IV) under water free conditions with a hydrogen halide in which formula $R^1$ signifies lower alkyl, $R^2$ signifies di-(lower alkyl)amino or a 5- or 6-membered —N-heterocyclyl group having the free valence bond at the nitrogen atom, and X signifies halogen.

18 Claims, No Drawings

PROCESS FOR THE MANUFACTURE OF 2,5-DISUBSTITUTED PYRIDINES

BACKGROUND OF THE INVENTION

Compounds of formula (I),

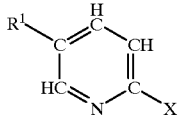
(I)

are known compounds and can be used in the preparation of endothelin receptor antagonists as disclosed in EP 0713875A1 and WO 96/19459 in which compounds such as pyridin-2-yl-carbamic acid 2-[6-(5-isopropyl-pyridine-2-sulfonylamino)-5-(2-methoxy-phenoxy)-2-morpholin-4-yl-pyrimidin-4-yloxy]-ethyl ester and 5-isopropyl-pyridine-2-sulfonic acid {6-(2-hydroxy-ethoxy)-5-(2-methoxy-phenoxy)-2-[2-(1H-tetrazol-5-yl)-pyridin-4-yl]-pyrimidin-4-yl}-amide are incorporated.

Processes for the preparation of 2-halogeno-5-alkylpyridines have been disclosed in, e.g. EP-A-0 584 491 and EP-A-0 162 464.

By the process of the present invention, 2-halo-5-lower alkyl pyridines can be obtained in better yields and in less reaction steps. The invention relates to a novel process for the preparation of 2,5-disubstituted pyridines. More particularly the invention relates to the preparation of 2-halo-5-lower alkyl pyridines of the formula (I)

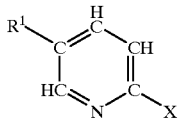
(I)

wherein
$R^1$ denotes lower alkyl, and
X denotes halogen.

SUMMARY OF THE INVENTION

According to the present invention, the compounds of formula (I) above can be prepared by a process which comprises the steps of a) reacting a compound of the formula (II)

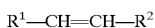
(II)

with an acrylic compound of the formula (III)

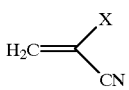
(III)

to form a compound of the formula (IV)

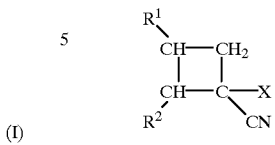
(IV)

and b) reacting the compound of formula (IV) under water free conditions with a hydrogen halide.

DETAILED DESCRIPTION OF THE INVENTION

As used herein, lower alkyl denotes straight-chain or branched $C_1$–$C_8$-alkyl for example methyl, ethyl, propyl, isopropyl, butyl, isobutyl, tert-butyl, the isomeric pentyls, the isomeric hexyls and the isomeric octyls.

As used herein, halogen denotes fluoro, chloro, bromo and iodo, with bromo and, chloro being preferred and with chloro being particularly preferred.

According to the present invention, the compounds of formula (I) above can be prepared by a process which comprises the steps of a) reacting a compound of the formula (II)

(II)

with an acrylic compound of the formula (III)

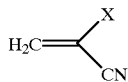
(III)

to form a compound of the formula (IV)

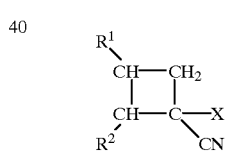
(IV)

and b) reacting the compound of formula (IV) under water free conditions with a hydrogen halide, in which formula:
$R^2$ is di-(lower alkyl)amino or a 5- or 6-membered —N-heterocyclyl group having the free valence bond at the nitrogen atom and,
$R^1$ is a lower alkyl, and
X is a halogen.

In a preferred embodiment, the invention is concerned with the preparation of compounds of formula (I), wherein $R^1$ is branched lower alkyl, particularly isopropyl, and X chlorine.

Examples of di-(lower alkyl)amino groups, when represented by $R^2$ are dimethyl amino, diethyl amino, dipropyl amino, diisopropyl amino, dibutyl amino, ethyl methyl amino, ethyl propyl amino, ethyl isopropyl amino, butyl ethyl amino, methyl propyl amino, isopropyl methyl amino, butyl methyl amino, butyl propyl amino, butyl isopropyl amino. The preferred di-(lower alkyl)amino group $R^2$ is diethyl amino.

Five or six membered —N-heterocyclyl groups, represented by $R^2$ may be substituted or unsubstituted and may contain additional heteroatoms such as N, O and S whereby the additional N atoms can be substituted by lower alkyl groups. Examples of such heterocyclyl groups are piperazine, pyrrole, pyrazole, imidazole, 1H-azepine, azetidine, aziridine. The heterocyclyl represented by $R^2$ is preferably pyrrolidine and piperidine and most preferably morpholine.

The following reaction steps a) and b) of the process of the invention can be carried out under water free conditions neat or preferably in the presence of a solvent.

Step a) of the process can be carried out in a solvent such as a halogenated hydrocarbon, ketone, nitrile, ester, ether, or alcohol or a mixture of these solvents. Examples of such solvents are dichloromethane, chloroform, dichloroethane, acetone, methyl ethyl ketone, cyclohexanone, acetonitrile, lower alkyl formiates, lower alkyl acetates, lower alkyl propionates, tetrahydrofuran, dioxane and lower alkyl alcohols. More preferred are the above mentioned solvents or a mixture thereof in the presence of an organic or inorganic water free acid such as alkane acids or halogen acids. Examples for such acids are HCl and especially acetic acid. Particularly preferred is the combination ethyl acetate/acetic acid and especially ethyl acetate containing 0.01–1.0 mol of acetic acid, and most preferred 0.03–0.1 mol acetic acid per mol of compound (III).

By using the mixtures of esters and acids mentioned under step a) no change of solvent is necessary throughout the entire process according to the invention. In step a), using a polymerisation inhibitor such as hydroquinone is preferred to prevent the polymerisation of the acrylic compound.

Step b) of the process can be carried out in a solvent which does not react with gaseous hydrogen halide such as halogenated hydrocarbons or esters or a mixtures thereof. Examples of such solvents are dichloromethane, chloroform, dichloroethane and lower alkyl formiates, lower alkyl acetates and lower alkyl propionates.

The reaction steps a) and b) may be carried out at room temperature or up to the boiling point of the used reactants and solvents. Higher temperatures are possible by using an autoclave.

In step b) the cyclobutane (IV) is treated under water free conditions with gaseous HX, preferably with gaseous HBr and particularly preferred with gaseous HCl whereupon a smooth conversion directly to (I) occurs. This reaction can be conducted in the solvents described above so that the formation of (IV) and its transformation to (I) can be carried out in one reaction chamber thus avoiding the necessity of isolating and purifying the compound of (IV) and the concomitant loss of material during handling. Purification of the product (I) is preferably effected by distillation.

In a preferred aspect, the invention is concerned with the above process, wherein step a) is carried out in an anhydrous solvent selected from halogenated hydrocarbons, ketones, nitrites, esters, ethers, alcohols or mixtures thereof, in the presence of a water-free acid. Particularly preferred is a mixture of ethyl acetate and acetic acid.

Preferred is also the above process, wherein in step b) the compound of formula (IV) is reacted in situ with gaseous HBr or HCl.

Another preferred aspect of the present invention is the above process, wherein $R^1$ is branched lower alkyl and particularly isopropyl.

Also particularly preferred is the above process, wherein X is chlorine.

Moreover, a preferred aspect of the present invention is the above process, wherein $R^2$ is morpholino.

Another preferred aspect of the present invention is the transformation of compounds of the formula (I) into endothelin receptor antagonists, especially endothelin receptor antagonists as disclosed in EP 0713875A1 and WO 96/19459 such as pyridin-2-yl-carbamic acid 2-[6-(5-isopropyl-pyridine-2-sulfonylamino)-5-(2-methoxy-phenoxy)-2-morpholin-4-yl-pyrimidin-4-yloxy]-ethyl ester and/or 5-isopropyl-pyridine-2-sulfonic acid {6-(2-hydroxy-ethoxy)-5-(2-methoxy-phenoxy)-2-[2-(1H-tetrazol-5-yl)-pyridin-4-yl]-pyrmidin-4-yl}-amide and/or 5-methyl-pyridine-2-sulfonic acid {6-(2-hydroxy-ethoxy)-5-(2-methoxy-phenoxy)-2-[2-(1H-tetrazol-5-yl)-pyridin-4-yl]-pyrimidin-4-yl}-amide. In general, this transformation can be effected by the following reactions: A 2-halopyridine is converted to a 2-pyridinethiol with an appropriate sulphur nucleophile derived from sulphides, hydrogensulphides, thio-carbonic, -sulphonic or -phosphoric acids or with thiourea. The 2-pyridinethiol is easily oxidised to the corresponding sulphonic acid which can be activated and transformed by standard procedures with ammonia to a sulphonamide. In the case of halogen oxidants, the intermediate sulphohalide, upon treatment with ammonia, provide a sulphonamide directly. Deprotonation of the pyridine-sulphonamide with a base and treatment of the salt thereof with various substituted 4,6-dihalopyrimidines furnish a pyridine-2-sulphonic acid 6-halo-pyrimidinyl-4-yl-amide. This is converted to pyridine-2-sulphonic acid 6-(2-hydroxyethoxy)-pyrimidinyl-4-yl-amide with ethylene glycol in the presence of a base. Subsequent reaction with pyridine-2-carbonyl azide delivers the final product class, pyridin-2-yl-carbamic acid 2-[6-pyridine-2-sulphonylamino)-pyrimidin-4-yloxy]ethyl ester (cf. EP 0713875A1).

This methodology is by no means restricted to the active substances described in EP 0713875A1 and can be applied to the preparation of other endothelin receptor antagonists such as those described in WO 96/19459.

Particularly preferred is the process as described as above, wherein 1-(N-morpholino)-3-(methyl)-but-1-ene is transformed into 2-chloro-5-isopropylpyridine by the following steps:

a) reaction with chloracylnitrile,
b) addition of hydrogen halide under water free conditions.

Also particularly preferred is the above process, wherein 2-chloro-5-isopropyl-pyridine is transformed into pyridin-2-yl-carbamic acid 2-[6-(5-isopropyl-pyridine-2-sulfonylamino)-5-(2-methoxy-phenoxy)-2-morpholin-4-yl-pyrimidin-4-yloxy]-ethyl ester by the following steps:

a) reaction with thiourea to form 5-isopropyl-pyridine-2-thiol,
b) reaction with chlorine to form 5-isopropyl-pyridine-2-sulfochloride,
c) reaction with ammonium hydroxide to form 5-isopropyl-pyridine-2-sulfonamide,
d) reaction with 4,6-dichloro-5-(2-methoxy-phenoxy)-2-morpholin-4-yl-pyrimidine to form 5-isopropyl-pyridine-2-sulfonic acid 6-chloro-5-(2-methoxy-phenoxy)-2-morpholin-4-yl-pyrimidin-4-yl-amide,
e) reaction with sodium in ethylene glycol to form 5-isopropyl-pyridine-2-sulfonic acid 6-(2-hydroxy-ethoxy)-5-(2-methoxy-phenoxy)-2-morpholin-4-yl-pyrimidin-4-yl-amide,
f) reaction with pyridine-2-carbonyl azide to form pyridin-2-yl-carbamic acid 2-[6-(5-isopropyl-pyridine-2-sulfonylamino)-5-(2-methoxy-phenoxy)-2-morpholin-4-yl-pyrimidin-4-yloxy]-ethyl ester.

Also particularly preferred is the above process, wherein 2-chloro-5-isopropyl-pyridine is transformed into 5-isopropyl-pyridine-2-sulfonic acid {6-(2-hydroxy-ethoxy)-5-(2-methoxy-phenoxy)-2-[2-(1H-tetrazol-5-yl)-pyridin-4-yl]-pyrimidin-4-yl}-amide by the following steps:
  a) reaction with thiourea to form 5-isopropyl-pyridine-2-thiol,
  b) reaction with chlorine to form 5-isopropyl-pyridine-2-sulfochloride,
  c) reaction with ammonium hydroxide to form 5-isopropyl-pyridine-2-sulfonamide,
  d) reaction with 4-[4,6-dichloro-5-(2-methoxy-phenoxy)-pyrimidin-2-yl]-pyridine-1-oxide to form 5-isopropyl-pyridine-2-sulfonic acid 6-chloro-5-(2-methoxy-phenoxy)-2-(1-oxy-pyridin-4-yl)-pyrimidin-4-yl amide,
  e) reaction with sodium in ethylene glycol to form 5-isopropyl-pyridine-2-sulfonic acid 6-(2-hydroxy-ethoxy)-5-(2-methoxy-phenoxy)-2-(1-oxy-pyridin-4-yl)-pyrimidin-4-yl amide,
  f) reaction with trimethylsilylcyanide and triethylamine to form 5-isopropyl-pyridine-2-sulphonic acid 2-(2-cyano-pyridin-4-yl)-6-(2-hydroxy-ethoxy)-5-(2-methoxy-phenoxy)-pyrimidin-4-yl-amide,
  g) reaction with ammonium chloride and sodium azide to form 5-isopropyl-pyridine-2-sulfonic acid {6-(2-hydroxy-ethoxy)-5-(2-methoxy-phenoxy)-2-[2-(1H-tetrazol-5-yl)-pyridin-4-yl]-pyrimidin-4-yl}-amide.

An additional aspect of the present invention is the above process, wherein 1-(N-morphohno)-prop-1-ene is transformed into 2-chloro-5-methyl-pyridine by the following steps:
  a) reaction with chloracylnitrile,
  b) addition of a hydrogen halide under water free conditions.

An additional aspect of the present invention is the above process, wherein 2-chloro-5-methyl-pyridine is transformed into 5-methyl-pyridine-2-sulfonic acid {6-(2-hydroxy-ethoxy)-5-(2-methoxy-phenoxy)-2-[2-(1H-tetrazol-5-yl)-pyridin-4-yl]-pyrimidin-4-yl}-amide by the following steps:
  a) reaction with thiourea to form 5-methyl-pyridine-2-thiol,
  b) reaction with chlorine to form 5-methyl-pyridine-2-sulfochloride,
  c) reaction with ammonium hydroxide to form 5-methyl-pyridine-2-sulfonamide,
  d) reaction with 4-[4,6-dichloro-5-(2-methoxy-phenoxy)-pyrimidin-2-yl]-pyridine-1-oxide to form 5-methyl-pyridine-2-sulfonic acid 6-chloro-5-(2-methoxy-phenoxy)-2-(1-oxy-pyridin-4-yl)-pyrimidin-4-yl amide,
  e) reaction with sodium in ethylene glycol to form 5-methyl-pyridine-2-sulfonic acid 6-(2-hydroxy-ethoxy)-5-(2-methoxy-phenoxy)-2-(1-oxy-pyridin-4-yl)-pyrimidin-4-yl amide,
  f) reaction with trimethylsilylcyanide and triethylamine to form 5-methyl-pyridine-2-sulphonic acid 2-(2-cyano-pyridin-4-yl)-6-(2-hydroxy-ethoxy)-5-(2-methoxy-phenoxy)-pyrimidin-4-yl-amide,
  g) reaction with ammonium chloride and sodium azide to form 5-methyl-pyridine-2-sulfonic acid {6-(2-hydroxy-ethoxy)-5-(2-methoxy-phenoxy)-2-[2-(1H-tetrazol-5-yl)-pyridin-4-yl]-pyrimidin-4-yl}-amide.

Also preferred is the use of the above process in the preparation of endothelin receptor antagonists such as 5-methyl-pyridine-2-sulfonic acid {6-(2-hydroxy-ethoxy)-5-(2-methoxy-phenoxy)-2-[2-(1H-tetrazol-5-yl)-pyridin-4-yl]-pyrimidin-4-yl}-amide and particularly preferred such as pyridin-2-yl-carbamic acid 2-[6-(5-isopropyl-pyridine-2-sulfonylamino)-5-(2-methoxy-phenoxy)-2-morpholin-4-yl-pyrimidin-4-yloxy]-ethyl ester and/or 5-isopropyl-pyridine-2 -sulfonic acid {6-(2-hydroxy-ethoxy)-5-(2-methoxy-phenoxy)-2-[2-(1H-tetrazol-5-yl)-pyridin-4-yl]-pyrimidin-4-yl}-amide.

Another preferred aspect of the present invention are the compounds as obtained by the above process.

EXAMPLE 3.54 l (32.7 mol) of 3-methylbutyraldehyde were added under argon atmosphere over a period of 60 minutes to a solution of 2.61 l (30 mol) morpholine in 25 l cyclohexane at 28° C. Additional 5 l cyclohexane were used to rinse the rest of 3-methylbutyraldehyde into the reaction mixture. The mixture was heated at 80° C. for 22 hours with azeotropic removal of water then evaporated at 45° C./180 mbar. 1.5 l of ethyl acetate were added and again removed under reduced pressure. The residue remaining was 1-(N-morpholino)-3-(methyl)-but-1-ene.

The 1-(N-morpholino)-3-(methyl)-but-1-ene obtained by the reaction above was dissolved in 30 l of ethyl acetate. After the addition of 0.18 l acetic acid and 0.012 kg hydroquinone, the mixture was brought to reflux at 78° C. The temperature was kept at 78° C. while 3.72 l (46.32 mol) chloracylnitrile was introduced over 1–2 hours. Stirring was continued at 78° C. for 1 hour and then at 75° C. for 3 hours while 1.59 kg HCl gas was introduced. The mixture was allowed to cool to 22° C. under an inert atmosphere and the pH was brought to 8 over 2 hours at 10° C. with 37 l of aqueous sodium hydrogen carbonate (3.6 kg) solution. After stirring at 21° C. for 15 min., the organic phase was separated and 2-chloro-5-isopropyl-pyridine was extracted twice with 15 l ethyl acetate and the combined extracts were washed twice with 15 l of sodium chloride solution (4.8 kg NaCl). The organic phase was evaporated at 45° C./25 mbar and the product was subjected to vacuum distillation (short column). 2-Chloro-5-isopropyl-pyridine distilled at 40–45° C./1 mbar. In this way a 60% overall yield of 2-chloro-5-isopropyl-pyridine from 3-methylbutyraldehyde was obtained.

The 2-chloro-5-isopropyl-pyridine can be converted to pyridin-2-yl-carbamic acid 2-[6-(5-isopropyl-pyridine-2-sulfonylamino)-5-(2-methoxy-phenoxy)-2-morpholin-4-yl-pyrimidin-4-yloxy]-ethyl ester or 5-isopropyl-pyridine-2-sulfonic acid {6-(2-hydroxy-ethoxy)-5-(2-methoxy-phenoxy)-2-[2-(1H-tetrazol-5-yl)-pyridin-4-yl]-pyrimidin-4-yl}-amide as follows:

2-Chloro-5-isopropyl-pyridine is transformed into 5-isopropyl-pyridine-2-thiol by reaction with thiourea in aqueous HCl. Chlorination of 5-isopropyl-pyridine-2-thiol with chlorine in acetic acid yields 5-isopropyl-pyridine-2-sulfochloride which is transformed into 5-isopropyl-pyridine-2-sulfonamide by treatment with aqueous ammonium hydroxide. The pyridinesulphonamide may then be deprotonated with a base to yield a salt thereof.

4,6-Dichloro-5-(2-methoxy-phenoxy)-2-morpholin-4-yl-pyrimidine is treated with 5-isopropyl-pyridine-2-sulfonamide potassium salt to form 5-isopropyl-pyridine-2-sulfonic acid 6-chloro-5-(2-methoxy-phenoxy)-2-morpholin-4-yl-pyrimidin-4-yl-amide. This compound is then added to a solution of sodium in ethylene glycol. After heating, 5-isopropyl-pyridine-2-sulfonic acid 6-(2-hydroxyethoxy)-5-(2-methoxy-phenoxy)-2-morpholin-4-yl-pyrimidin-4-yl-amide is obtained and then added to a solution of pyridine-2-carbonyl azide in dioxane to form pyridin-2-yl-carbamic acid 2-[6-(5-isopropyl-pyridine-2-sulfonylamino)-5-(2-methoxy-phenoxy)-2-morpholin-4-yl-pyrimidin-4-yloxy]-ethyl ester (see EP 0713875A1).

4-Cyano-pyridine is transformed into 4-amidino-pyridine hydrochloride by reaction of 4-cyano-pyridine with a solution of sodium in methanol followed by the addition of ammonium chloride.

Diethyl-(2-methoxy-phenoxy)malonate is dissolved in a solution of sodium in methanol. Thereafter 4-amidino-pyridine hydrochloride is added to obtain 5-(2-methoxy-phenoxy)-2-(pyridin-4-yl)-pyrimidin-4,6-diol (or a tautomeric derivative). This compound is heated with phosphorus oxychloride to yield 4,6-dichloro-5-(2-methoxy-phenoxy)-2-pyridin-4-yl)-pyrimidine which is boiled with peracetic acid to obtain 4-[4,6-dichloro-5-(2-methoxy-phenoxy)-pyrimidin-2-yl]-pyridine-1-oxide. By reaction of this compound with 5-isopropyl-pyridine-2-sulfonamide potassium there is obtained 5-isopropyl-pyridine-2-sulfonic acid 6-chloro-5-(2-methoxy-phenoxy)-2-(1-oxy-pyridin-4-yl)-pyrimidin-4-yl amide which is added as a solution in dimethoxyethane to a solution of sodium in ethylene glycol. 5-Isopropyl-pyridine-2-sulfonic acid 6-(2-hydroxy-ethoxy)-5-(2-methoxy-phenoxy)-2-(1-oxy-pyridin-4-yl)-pyrimidin-4-yl amide is obtained which is heated with trimethylsilyl-cyanide and triethylamine in acetonitrile to obtain 5-isopropyl-pyridine-2-sulphonic acid 2-(2-cyano-pyridin-4-yl)-6-(2-hydroxy-ethoxy)-5-(2-methoxy-phenoxy)-pyrimidin-4-yl-amide. This is then heated with ammonium chloride and sodium azide in dimethyl formamide to yield 5-isopropyl-pyridine-2-sulfonic acid {6-(2-hydroxy-ethoxy)-5-(2-methoxy-phenoxy)-2-[2-(1H-tetrazol-5-yl)-pyridin-4-yl]-pyrimidin-4-yl}-amide (see WO 96/19459).

What is claimed is:

1. Process for the preparation of a 2,5-disubstituted pyridine of the formula (I)

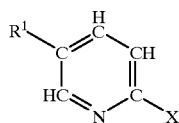
(I)

comprising:

a) reacting a compound of the formula (II)

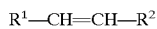
(II)

with an acrylic compound of the formula (III)

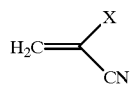
(III)

to form a compound of the formula (IV)

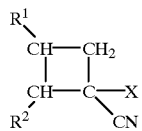
(IV)

and b) reacting the compound of formula (IV) under water free conditions with a hydrogen halide, wherein $R^1$ signifies lower alkyl, $R^2$ signifies di-(lower alkyl)amino or a 5- or 6-membered —N-heterocyclyl group having the free valence bond at the nitrogen atom, and X signifies a halogen.

2. Process according to claim 1, wherein step a) is carried out in a anhydrous solvent selected from the group consisting of halogenated hydrocarbons, ketones, nitriles, esters, ethers, alcohols and mixtures thereof, in the presence of a water-free acid.

3. Process according to claim 2, wherein the solvent is a mixture of ethyl acetate and acetic acid.

4. Process according to claim 2, wherein in step b) the compound of formula (IV) is reacted in situ with gaseous HBr or Hcl.

5. Process according to claim 3, wherein in step b) the compound of formula (IV) is reacted in situ with gaseous HBr or HCl.

6. Process according to claim 4, wherein $R^1$ is branched lower alkyl.

7. Process according to claim 5, wherein $R^1$ is branched lower alkyl.

8. Process according to claim 6, wherein $R^1$ is isopropyl.

9. Process according to claim 7, wherein $R^1$ is isopropyl.

10. Process according to claim 8, wherein X is chlorine.

11. Process according to claim 9, wherein X is chlorine.

12. Process according to claim 10, wherein $R^2$ is morpholino.

13. Process according to claim 11, wherein $R^2$ is morpholino.

14. Process according to claim 1, characterised in that 1-(N-morpholino)-3-(methyl)-but-1-ene is transformed into 2-chloro-5-isopropyl-pyridine by the steps comprising:

a) reacting 1-(N-morpholino)-3-(methyl)-but-1-ene with chloracylnitrile, and b) addition of hydrogen halide under water free conditions.

15. Process according to claim 14, wherein the 2-chloro-5-isopropyl-pyridine is transformed into pyridin-2-yl-carbamic acid 2-[6-(5-isopropyl-pyridine-2-sulfonylamino)-5-(2-methoxy-phenoxy)-2-morpholin-4-yl-pyrimidin-4-yloxy]-ethyl ester by the further following steps:

a) reacting 2-chloro-5-isopropyl-pyridine with thiourea to form 5-isopropyl-pyridine-2-thiol, b) reacting the product of step a) with chlorine to form 5-isopropyl-pyridine-2-sulfochloride, c) reacting the product of step b) with ammonium hydroxide to form 5-isopropyl-pyridine-2-sulfonamide, d) reacting the product of step c) with 4,6-dichloro-5-(2-methoxy-phenoxy)-2-morpholin-4-yl-pyrimidine to form 5-isopropyl-pyridine-2-sulfonic acid 6-chloro-5-(2-methoxy-phenoxy)-2-morpholin-4-yl-pyrimidin-4-yl-amide, e) reacting the product of step d) with sodium in ethylene glycol to form 5-isopropyl-pyridine-2-sulfonic acid 6-(2-hydroxy-ethoxy)-5-(2-methoxy-phenoxy)-2-morpholin-4-yl-pyrimidin-4-yl-amide, and f) reacting the product of step e) with pyridine-2-carbonyl azide to form pyridin-2-yl-carbamic acid 2-[6-(5-isopropyl-pyridine-2-sulfonylamino)-5-(2-methoxy-phenoxy)-2-morpholin-4-yl-pyrimidin-4-yloxy]-ethyl ester.

16. Process according to claim 14, wherein the 2-chloro-5-isopropyl-pyridine is transformed into 5-isopropyl-pyridine-2-sulfonic acid {6-(2-hydroxy-ethoxy)-5-(2-methoxy-phenoxy)-2-[2-(1H-tetrazol-5-yl)-pyridin-4-yl]-pyrmidin-4-yl}-amide by the following further steps:

a) reacting 2-chloro-5-isopropyl-pyridine with thiourea to form 5-isopropyl-pyridine-2-thiol, b) reacting the product of step a) with chlorine to form 5-isopropyl-pyridine-2-sulfochloride, c) reacting the product of step b) with ammonium hydroxide to form 5-isopropyl-pyridine-2-sulfonamide, d) reacting the product of step c) with 4-[4,6-dichloro-5-(2-methoxy-phenoxy)-pyrimidin-2-yl]-pyridine-1-oxide to form 5-isopropyl-pyridine-2-sulfonic acid 6-chloro-5-(2-methoxy-phenoxy)-2-(1-oxy-pyridin-4-yl)-pyrimidin-4-yl amide, e) reacting the product of step d) with sodium in ethylene glycol to form 5-isopropyl-pyridine-2-sulfonic acid 6-(2-hydroxy-ethoxy)-5-(2-methoxy-phenoxy)-2-(1-oxy-pyridin-4-yl)-pyrimidin-4-yl amide, f) reacting the product of step e) with trimethylsilylcyanide and triethylamine to form 5-isopropyl-pyridine-2-sulphonic acid 2-(2-cyano-pyridin-4-yl)-6-(2-hydroxy-ethoxy)-5-(2-methoxy-phenoxy)-pyrimidin-4-yl-amide, and g) reacting the product of step f) with ammonium chloride and sodium azide to form 5-isopropyl-pyridine-2-sulfonic acid {6-(2-hydroxy-ethoxy)-5-(2-methoxy-phenoxy)-2-[2-(1H-tetrazol-5-yl)-pyridin-4-yl]-pyrimidin-4-yl}-amide.

17. Process according to claim 1, characterised in that 1-(N-morpholino)-prop-1-ene is transformed into 2-chloro-5-methyl-pyridine by the steps comprising:

a) reaction with chloracylnitrile, and b) addition of a hydrogen halide under water free conditions.

18. Process according to claim 17, wherein the 2-chloro-5-methyl-pyridine is transformed into 5-methyl-pyridine-2-sulfonic acid {6-(2-hydroxy-ethoxy)-5-(2-methoxy-phenoxy)-2-[2-(1H-tetrazol-5-yl)-pyridin-4-yl]-pyrimidin-4-yl}-amide by the following further steps:

a) reacting 2-chloro-5-methyl-pyridine with thiourea to form 5-methyl-pyridine-2-thiol, b) reacting the product of step a) with chlorine to form 5-methyl-pyridine-2-sulfochloride, c) reacting the product of step b) with ammonium hydroxide to form 5-methyl-pyridine-2-sulfonamide, d) reacting the product of step c) with 4-[4,6-dichloro-5-(2-methoxy-phenoxy)-pyrimidin-2-yl]-pyridine-1-oxide to form 5-methyl-pyridine-2-sulfonic acid 6-chloro-5-(2-methoxy-phenoxy)-2-(1-oxy-pyridin-4-yl)-pyrimidin-4-yl amide, e) reacting the product of step d) with sodium in ethylene glycol to form 5-methyl-pyridine-2-sulfonic acid 6-(2-hydroxy-ethoxy)-5-(2-methoxy-phenoxy)-2-(1-oxy-pyridin-4-yl)-pyrimidin-4-yl amide, f) reacting the product of step e) with trimethylsilylcyanide and triethylamine to form 5-methyl-pyridine-2-sulphonic acid 2-(2-cyano-pyridin-4-yl)-6-(2-hydroxy-ethoxy)-5-(2-methoxy-phenoxy)-pyrimidin-4-yl-amide, and g) reacting the product of step f) with ammonium chloride and sodium azide to form 5-methyl-pyridine-2-sulfonic acid {6-(2-hydroxy-ethoxy)-5-(2-methoxy-phenoxy)-2-[2-(1H-tetrazol-5-yl)-pyridin-4-yl]-pyrimidin-4-yl}-amide.

* * * * *

UNITED STATES PATENT AND TRADEMARK OFFICE
CERTIFICATE OF CORRECTION

PATENT NO. : 6,080,866
DATED : June 27, 2000
INVENTOR(S) : Paul Spurr

It is certified that error appears in the above-identified patent and that said Letters Patent is hereby corrected as shown below:

In claim 2, column 8, line 21, delete "nitrites," and insert -- nitriles, --.

Signed and Sealed this

Third Day of April, 2001

Attest:

NICHOLAS P. GODICI

Attesting Officer     *Acting Director of the United States Patent and Trademark Office*